US008974651B2

(12) United States Patent
Chan et al.

(10) Patent No.: US 8,974,651 B2
(45) Date of Patent: Mar. 10, 2015

(54) ILLUMINATOR FOR VISUALIZATION OF FLUOROPHORES

(75) Inventors: Richard Chan, La Jolla, CA (US);
Winston Glenn Walker, Littleton, CO (US); Rita M. Wong, San Diego, CA (US); Jason In, San Diego, CA (US)

(73) Assignee: C.C. IMEX, San Diego, CA (US)

( * ) Notice: Subject to any disclaimer, the term of this patent is extended or adjusted under 35 U.S.C. 154(b) by 618 days.

(21) Appl. No.: 13/088,390

(22) Filed: Apr. 17, 2011

(65) Prior Publication Data

US 2011/0253541 A1    Oct. 20, 2011

Related U.S. Application Data

(60) Provisional application No. 61/325,305, filed on Apr. 17, 2010.

(51) Int. Cl.
*G01N 27/447* (2006.01)

(52) U.S. Cl.
CPC .................. *G01N 27/44721* (2013.01)
USPC .......................................... 204/461; 204/612

(58) Field of Classification Search
USPC ......... 204/456, 450, 461, 466, 600, 606, 612, 204/616–618; 356/344, 432–444
See application file for complete search history.

(56) References Cited

U.S. PATENT DOCUMENTS

| | | |
|---|---|---|
| 4,005,286 A * | 1/1977 | Faulkner ........................ 250/216 |
| 4,520,110 A | 5/1985 | Stryer et al. |
| 4,542,104 A | 9/1985 | Stryer et al. |
| 4,603,209 A | 7/1986 | Tsien et al. |
| 4,657,655 A | 4/1987 | Smoot et al. |
| 4,714,763 A | 12/1987 | Theodoropulos |
| 4,774,339 A | 9/1988 | Haugland et al. |
| 4,786,813 A | 11/1988 | Svanberg et al. |
| 4,810,636 A | 3/1989 | Corey |
| 4,812,409 A | 3/1989 | Babb et al. |
| 4,849,362 A | 7/1989 | DeMarinis et al. |
| 4,859,582 A | 8/1989 | Stryer et al. |
| 4,883,867 A | 11/1989 | Lee et al. |
| 4,908,112 A | 3/1990 | Pace |
| 4,945,171 A | 7/1990 | Haugland et al. |
| 4,957,870 A | 9/1990 | Lee et al. |
| 4,981,977 A | 1/1991 | Southwick et al. |
| 5,055,556 A | 10/1991 | Stryer et al. |
| 5,061,336 A | 10/1991 | Soane |
| 5,071,531 A | 12/1991 | Soane |
| 5,132,012 A | 7/1992 | Miura et al. |
| 5,132,432 A | 7/1992 | Haugland et al. |
| 5,135,627 A | 8/1992 | Soane |
| 5,187,288 A | 2/1993 | Kang et al. |
| 5,194,133 A | 3/1993 | Clark et al. |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |

(Continued)

*Primary Examiner* — Luan Van
*Assistant Examiner* — Gurpreet Kaur
(74) *Attorney, Agent, or Firm* — John L. Rogitz

(57) ABSTRACT

The present invention discloses apparatuses and methods for the visualization of fluorophores in biological systems such as electrophoresis gels and cell cultures. Preferred embodiments of the apparatuses consists of a tray or tank having one or more light sources disposed to direct light through an electrophoresis gel disposed within the vessel such that the luminescence from fluorophores in the gel are easily visualized.

19 Claims, 6 Drawing Sheets

(56) References Cited

U.S. PATENT DOCUMENTS

| | | |
|---|---|---|
| 5,314,805 A | 5/1994 | Haugland et al. |
| 5,327,195 A | 7/1994 | Ehr |
| 5,347,342 A | 9/1994 | Ehr |
| 5,363,854 A | 11/1994 | Martens |
| 5,410,030 A | 4/1995 | Yue et al. |
| 5,433,896 A | 7/1995 | Kang et al. |
| 5,436,134 A | 7/1995 | Haugland et al. |
| 5,442,045 A | 8/1995 | Haugland et al. |
| 5,449,446 A | 9/1995 | Verma et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,507,287 A | 4/1996 | Palcic et al. |
| 5,534,416 A | 7/1996 | Millard et al. |
| 5,569,364 A | 10/1996 | Hooper et al. |
| 5,569,587 A | 10/1996 | Waggoner |
| 5,569,766 A | 10/1996 | Waggoner et al. |
| 5,571,410 A | 11/1996 | Swedberg et al. |
| 5,580,990 A | 12/1996 | van den Berg et al. |
| 5,582,702 A | 12/1996 | Cabilly et al. |
| 5,582,977 A | 12/1996 | Yue et al. |
| 5,605,662 A | 2/1997 | Heller et al. |
| 5,606,502 A | 2/1997 | Adachi et al. |
| 5,616,502 A | 4/1997 | Haugland et al. |
| 5,627,027 A | 5/1997 | Waggoner |
| 5,631,337 A | 5/1997 | Sassi et al. |
| 5,647,368 A | 7/1997 | Zeng et al. |
| 5,658,751 A | 8/1997 | Yue et al. |
| 5,696,157 A | 12/1997 | Wang et al. |
| 5,770,365 A | 6/1998 | Lane et al. |
| 5,798,276 A | 8/1998 | Haugland et al. |
| 5,800,690 A | 9/1998 | Chow et al. |
| 5,808,044 A | 9/1998 | Brush et al. |
| 5,824,204 A | 10/1998 | Jerman |
| 5,830,912 A | 11/1998 | Gee et al. |
| 5,846,737 A | 12/1998 | Kang |
| 5,863,753 A | 1/1999 | Haugland et al. |
| 5,865,974 A | 2/1999 | Cabilly et al. |
| 5,877,310 A | 3/1999 | Reddington et al. |
| 5,929,208 A | 7/1999 | Heller et al. |
| 6,001,229 A | 12/1999 | Ramsey |
| 6,002,003 A | 12/1999 | Shen et al. |
| 6,004,536 A | 12/1999 | Leung et al. |
| 6,008,373 A | 12/1999 | Waggoner et al. |
| 6,008,379 A | 12/1999 | Benson et al. |
| 6,017,696 A | 1/2000 | Heller |
| 6,043,025 A | 3/2000 | Minden et al. |
| 6,051,380 A | 4/2000 | Sosnowski et al. |
| 6,127,134 A | 10/2000 | Minden et al. |
| 6,130,094 A | 10/2000 | Waggoner et al. |
| 6,130,101 A | 10/2000 | Mao et al. |
| 6,133,038 A | 10/2000 | Houthoff et al. |
| 6,133,445 A | 10/2000 | Waggoner et al. |
| 6,162,931 A | 12/2000 | Gee et al. |
| 6,198,107 B1 | 3/2001 | Seville |
| 6,210,896 B1 | 4/2001 | Chan |
| 6,238,624 B1 | 5/2001 | Heller et al. |
| 6,245,508 B1 | 6/2001 | Heller et al. |
| 6,258,606 B1 | 7/2001 | Kovacs |
| 6,270,641 B1 | 8/2001 | Griffiths et al. |
| 6,284,117 B1 | 9/2001 | Smolko et al. |
| 6,290,909 B1 | 9/2001 | Paul et al. |
| 6,309,601 B1 | 10/2001 | Juncosa et al. |
| 6,315,953 B1 | 11/2001 | Ackley et al. |
| 6,316,608 B1 | 11/2001 | Reynolds et al. |
| 6,339,392 B1 | 1/2002 | Ashihara |
| 6,355,420 B1 | 3/2002 | Chan |
| 6,379,516 B1 | 4/2002 | Cabilly et al. |
| 6,403,311 B1 | 6/2002 | Chan |
| 6,403,367 B1 | 6/2002 | Cheng et al. |
| 6,428,667 B1 | 8/2002 | Glazer et al. |
| 6,472,443 B1 | 10/2002 | Shepodd |
| 6,475,364 B1 | 11/2002 | Dubrow et al. |
| 6,499,499 B2 | 12/2002 | Dantsker et al. |
| 6,512,236 B2 | 1/2003 | Seville |
| 6,518,022 B1 | 2/2003 | Sosnowski et al. |
| 6,551,784 B2 | 4/2003 | Fodor et al. |
| 6,562,632 B1 | 5/2003 | Szalecki et al. |
| 6,567,163 B1 | 5/2003 | Sandstrom |
| 6,582,660 B1 | 6/2003 | Heller et al. |
| 6,613,525 B2 | 9/2003 | Nelson et al. |
| 6,660,480 B2 | 12/2003 | Ramsey et al. |
| 6,664,047 B1 | 12/2003 | Haugland et al. |
| 6,664,104 B2 | 12/2003 | Pourahmadi et al. |
| 6,716,979 B2 | 4/2004 | Diwu et al. |
| 6,726,880 B1 | 4/2004 | Ackley et al. |
| 6,914,250 B2 | 7/2005 | Seville |
| 6,967,251 B2 | 11/2005 | Haugland et al. |
| 6,974,873 B2 | 12/2005 | Leung et al. |
| 6,977,305 B2 | 12/2005 | Leung et al. |
| 7,524,672 B2 * | 4/2009 | West et al. .................. 435/287.2 |
| 8,562,802 B1 * | 10/2013 | Beaudet et al. ............... 204/466 |
| 2001/0008212 A1 | 7/2001 | Shepodd et al. |
| 2001/0052976 A1 | 12/2001 | Juncosa et al. |
| 2002/0004204 A1 | 1/2002 | O'Keefe |
| 2002/0028503 A1 | 3/2002 | Ackley et al. |
| 2002/0058273 A1 | 5/2002 | Shipwash |
| 2002/0064794 A1 | 5/2002 | Leung et al. |
| 2002/0064800 A1 | 5/2002 | Sando et al. |
| 2002/0089658 A1 | 7/2002 | Sevill |
| 2002/0095073 A1 | 7/2002 | Jacobs et al. |
| 2002/0112960 A1 | 8/2002 | Cabilly et al. |
| 2002/0127565 A1 | 9/2002 | Cunningham et al. |
| 2002/0131899 A1 | 9/2002 | Kovacs |
| 2002/0134680 A1 | 9/2002 | Cabilly et al. |
| 2002/0155586 A1 | 10/2002 | Cheng et al. |
| 2002/0164628 A1 | 11/2002 | Kurn |
| 2002/0194909 A1 | 12/2002 | Hasselbrink, Jr. et al. |
| 2003/0027354 A1 | 2/2003 | Geli |
| 2003/0048933 A1 | 3/2003 | Brown et al. |
| 2003/0075491 A1 | 4/2003 | Griffiths |
| 2003/0082604 A1 | 5/2003 | Swanson et al. |
| 2003/0104386 A1 | 6/2003 | Kuhr et al. |
| 2003/0146100 A1 | 8/2003 | Huang et al. |
| 2003/0151735 A1 | 8/2003 | Blumenfeld et al. |
| 2003/0175947 A1 | 9/2003 | Liu et al. |
| 2004/0011650 A1 | 1/2004 | Zenhausern et al. |
| 2004/0052929 A1 | 3/2004 | Kirby et al. |
| 2004/0126279 A1 | 7/2004 | Renzi et al. |
| 2004/0171034 A1 | 9/2004 | Agnew et al. |
| 2005/0074796 A1 | 4/2005 | Yue et al. |
| 2005/0082168 A1 | 4/2005 | Kang |
| 2005/0095602 A1 | 5/2005 | West et al. |
| 2005/0121325 A1 | 6/2005 | Updyke et al. |
| 2005/0208534 A1 | 9/2005 | Dallwig et al. |
| 2005/0214810 A1 | 9/2005 | Dallwig et al. |
| 2005/0244976 A1 | 11/2005 | Gee et al. |
| 2006/0030026 A1 * | 2/2006 | Garcia .................. 435/287.1 |
| 2006/0141554 A1 | 6/2006 | Gee et al. |

* cited by examiner

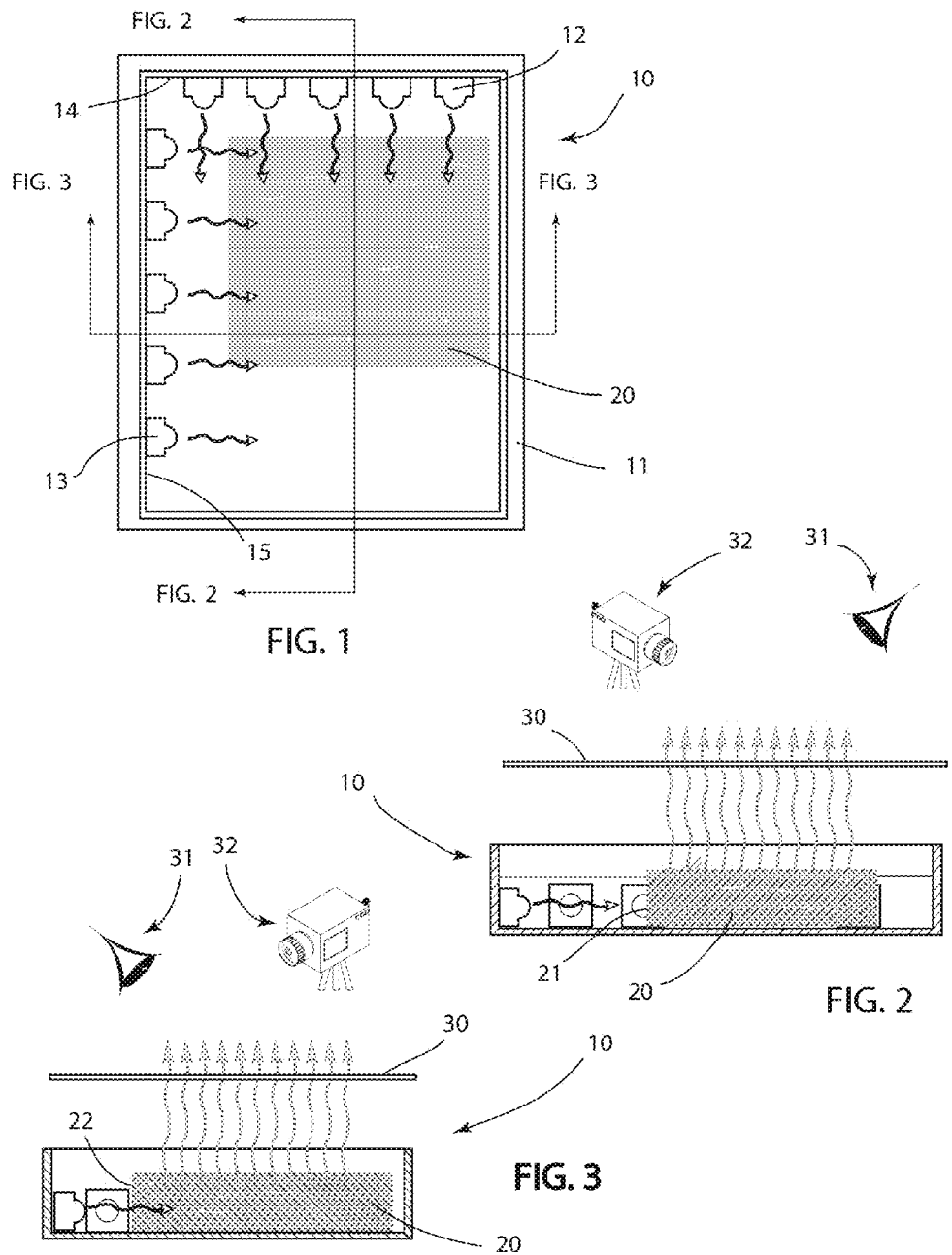

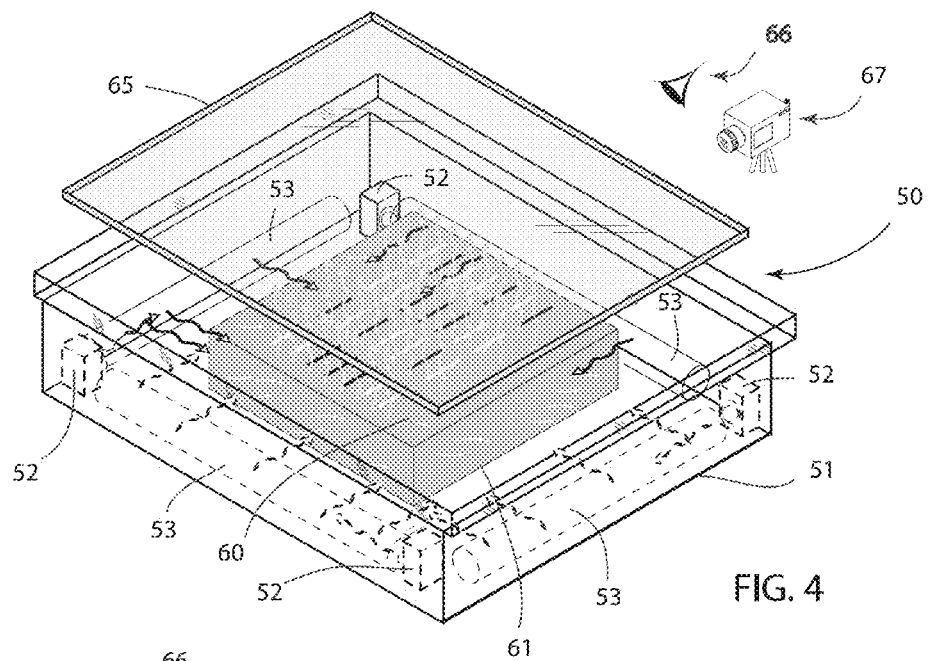
FIG. 4
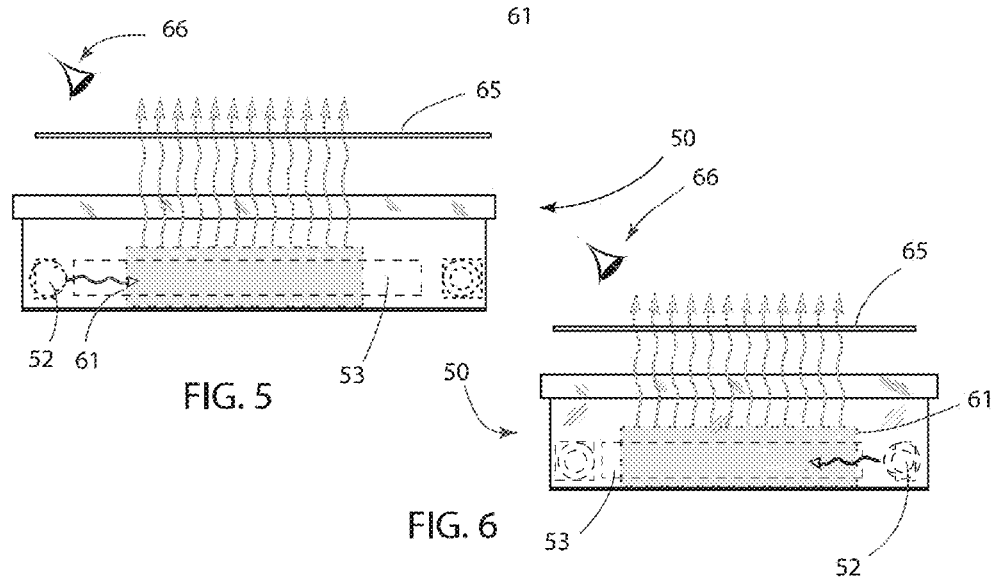
FIG. 5
FIG. 6

ILLUMINATOR FOR VISUALIZATION OF FLUOROPHORES

RELATED APPLICATION DATA

This application claims priority under 35 U.S.C. §119(e) to U.S. Provisional Application Ser. No. 61/325,305 filed Apr. 17, 2010.

FIELD OF THE INVENTION

The present invention relates to apparatuses and methods for the visualization of fluorophores in biological systems.

BACKGROUND

Gel electrophoresis is a technique used for the separation of deoxyribonucleic acid (DNA), ribonucleic acid (RNA), or protein molecules using an electric field applied to a gel matrix. DNA Gel electrophoresis is performed for analytical and preparative purposes, often after amplification of DNA via polymerase chain reaction (PCR) or restriction digest of DNA and as a preparative technique prior to use of other methods such as mass spectrometry, RFLP, PCR, cloning, DNA sequencing, or Southern blotting for further characterization.

Generally, after the separation by electrophoresis is complete, the molecules in the gel can be stained to make them visible. Common reagents such as ethidium bromide, GelRedm Sybr Green, Sybr Safe, Gel Green, silver, or Coomassie "blue dye" may be used for this process. Other methods may also be used to visualize the separation of the mixture's components on the gel. If the analyte molecules fluoresce under ultraviolet light, a photograph can be taken of the gel under ultraviolet lighting conditions. If the molecules to be separated contain radioactivity added for visibility, an autoradiogram can be recorded of the gel.

Illuminators useful for visualization of fluorophores are known in the art. For example, U.S. Pat. No. 5,347,342 discloses a transilluminator with UV light enclosed in a housing having a UV-transmissible window and a means for reflecting an image of the UV light source through the window in a manner that causes the UV light source to appear to be a multiple light source, while U.S. Pat. No. 5,327,195 describes a transilluminator with a UV light source enclosed in a housing having a UV-transmissible window with a removable protector plate overlying the window. U.S. Pat. No. 5,363,854 describes an apparatus for detecting anomalies of the skin by utilizing light in an ultraviolet wavelength range during a first time interval and with light in a visible wavelength range during a second time interval. U.S. Pat. Nos. 6,198,107, 6,512,236 and 6,914,250 describes a transilluminator system for viewing fluorescently stained DNA, protein or other biological material with a light source that requires at least two optical filters wherein a first optical filter is disposed between the light source and the fluorescent material being viewed and a second optical filter disposed between the fluorescing material and the viewer. The complete disclosure content of all patents and publications mentioned above are incorporated into this application by way of reference.

Therefore a need exists for apparatus and methods that utilize UV or visible light for the visualization of fluorophores wherein the apparatuses and methods require no optical filter between the light source and the fluorescent material being viewed; are compact or easily portable; and are adaptable to a variety of environments such as gel electrophoreses, cell-culture gels and the like.

BRIEF DESCRIPTION OF THE DRAWINGS

FIG. 1 is an orthogonal top view of an embodiment of an apparatus of the invention with a gel disposed therein.

FIG. 2 is an orthogonal side top view of the apparatus depicted in FIG. 1.

FIG. 3 is an orthogonal end top view of the apparatus depicted in FIG. 1.

FIG. 4 is an isometric view of an apparatus of the invention comprising four light sources disposed in the corners of a vessel.

FIG. 5 is an orthogonal side view of the apparatus depicted in FIG. 4.

FIG. 6 is an orthogonal end view of the apparatus depicted in FIG. 4

SUMMARY OF THE INVENTION

Figure 7:
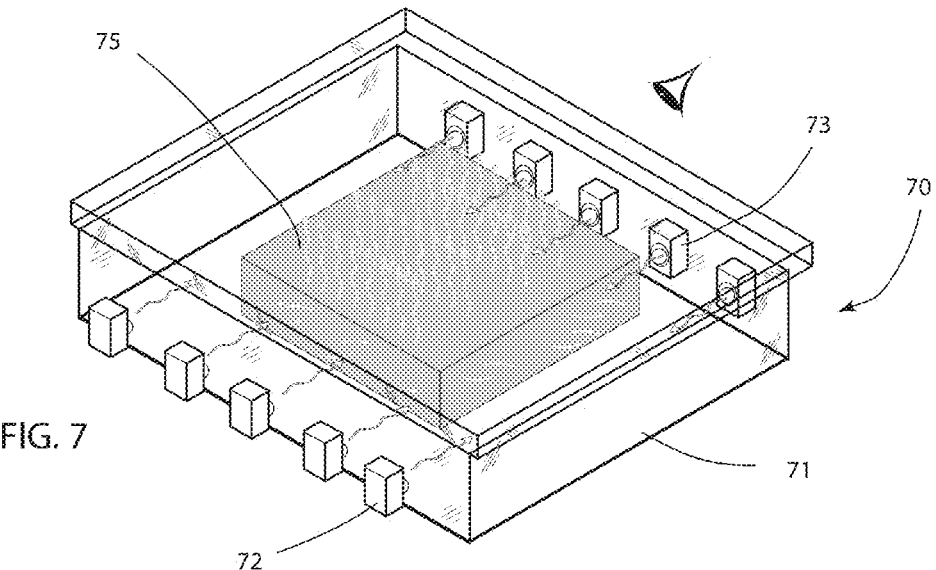
FIG. 7 is an isometric view of an apparatus of the invention suitable for electrophoreses procedures.
Figure 8:
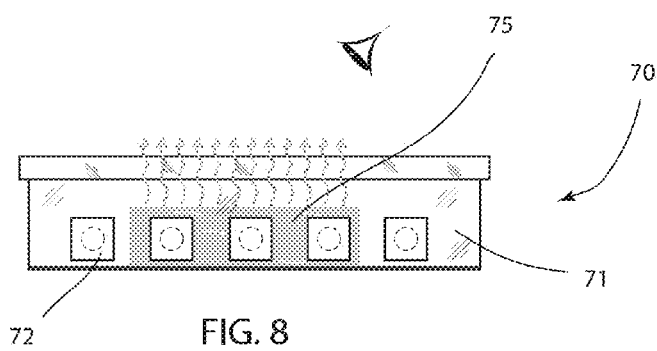
FIG. 8 is an orthogonal side view of the apparatus depicted in FIG. 7.
Figure 9:
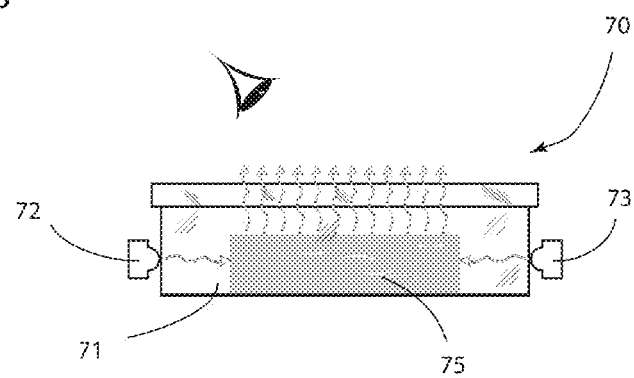
FIG. 9 is an orthogonal end view of the apparatus depicted in FIG. 7.
Figure 10A:
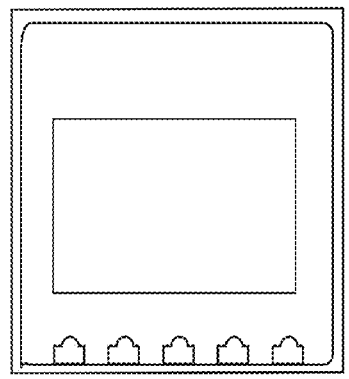
FIGS. 10 a-e present diagrammatic depictions of the disposition of light arrays for certain embodiments of the present invention.
Figure 10B:
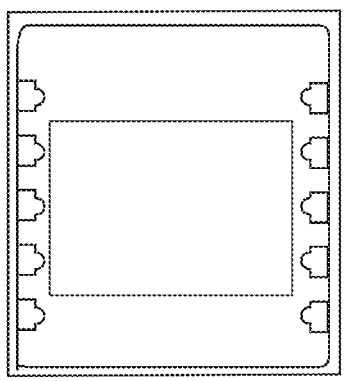
Figure 10C:
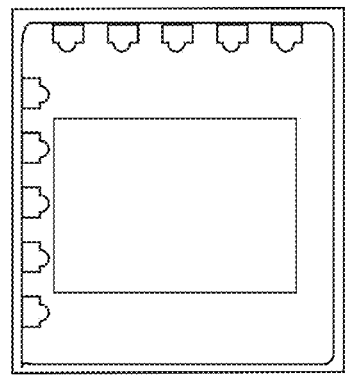
Figure 10D:
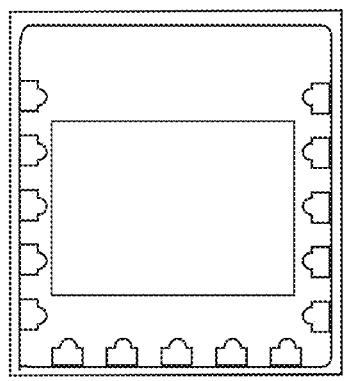
Figure 10E:
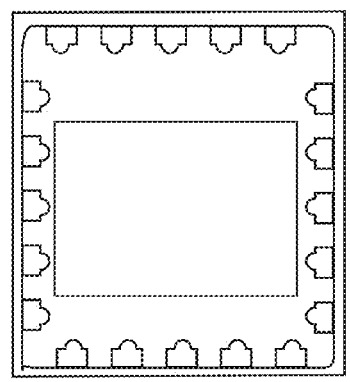
Figure 11A:
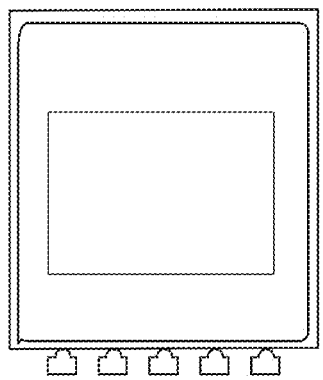
FIGS. 11 a-e present diagrammatic depictions of the disposition of light arrays for certain embodiments of the present invention.
Figure 11B:
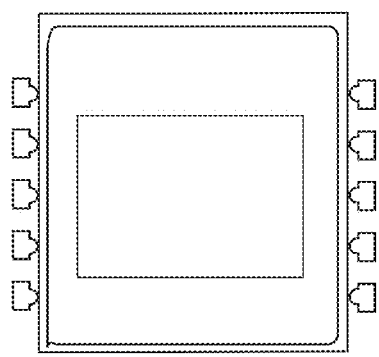
Figure 11C:
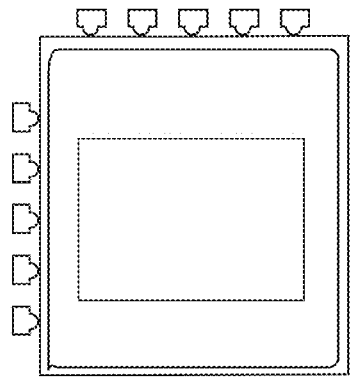
Figure 11D:
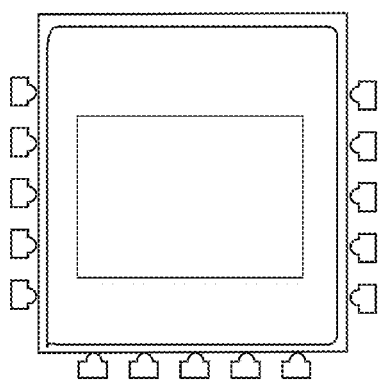
Figure 11E:
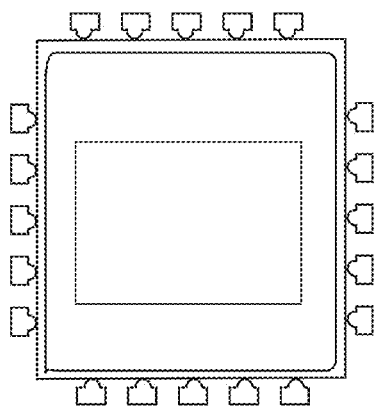

Apparatuses and methods of the present invention are useful for the visualization of fluorophores in biological systems including electrophoresis gels, cell cultures and the like.

Certain embodiments consist of a vessel in the form of a tray or tank having a polygon shaped base with a horizontal flat inner surface and vertical sides equal in number to the number of edges of the polygon, wherein each side is attached to an edge of the base to be orthogonal to the plane of the base, wherein each side has an inner surface and wherein the vessel is dimensioned to contain an electrophoresis gel comprising a flat gel top surface coplanar with a flat gel bottom surface and gel edges disposed orthogonally to the plane of the top and bottom surfaces. In such embodiments at least one light source is attached to the inner surface of a vessel side and the light source is positioned to illuminate an electrophoresis gel disposed within the vessel and wherein the light source provides one or more of the excitation wavelengths required effect the emission of fluorescence by fluorophores contained within a gel disposed within the vessel such that the fluorescence can be visualized by a viewer or an optical instrument suitable for such visualization.

In certain embodiments one or more optical filters can be disposed between the fluorescence emitting gel and the viewer or the optical instrument wherein the optical filter functions to aid in visualization of fluorescence emitted from the gel.

In certain embodiments the light source is a visible light source, while in other embodiments the light source is a UV light source. Certain other embodiments may employ combinations of visible and UV light sources. In certain preferred embodiments the light source comprises or more light-emitting diodes.

In certain embodiments the shape of the polygon shaped base is similar to the shape of the base of the gel disposed and viewed therein.

In certain embodiments of the apparatus the vessel has a polygon shaped base is a rectangular base. In these rectangular configurations light sources may be disposed along one, two, three or all four of the sides of the rectangular vessel. In embodiments wherein light sources are disposed along two sides of a rectangular vessel the two sides may be adjacent or opposing sides.

Certain embodiments comprising at least one light guide positioned in proximity to at least one light source wherein the light guide diffuses light emitted by the light source evenly across the edges of the gel being viewed.

In certain embodiment the edge of the gel is directly illuminated and functions as a light guide.

In preferred embodiments one or more the edge of the gel is illuminated, while in other embodiments the gel is illuminated on the lower surface, either from a backlight light guide or by direct illumination from a defuse source and in yet other embodiments the top surface of the gel is illuminated.

Further embodiments of apparatuses of the present have the form a vessel in the form of a tray or tank with rectangular vessel base having flat inner surface and four vertical walls, wherein each wall has an inner surface defining four corners and wherein the vessel is dimensioned to contain an electrophoresis gel having flat parallel top and bottom gel surfaces and gel edges disposed orthogonally to the plane of the top and bottom surfaces. Such embodiments have at least one light source disposed in a of the vessel wherein the light source(s) is positioned to illuminate an electrophoresis gel disposed within the vessel. In certain preferred embodiments each light source emits light through a suitably disposed light guide beginning at the light source, extending longitudinally along the inner surface of a vessel wall to a terminus at or near an adjacent inner corner such that the light emitted by the light source is diffused by the light guide to evenly illuminate an edge of a gel disposed within the vessel. In certain embodiments the light guides include, but are not limited to, the readily available light guides such as tubular or rod like guides, fiber optic bundles and the like that are well known in the art.

In certain embodiments a rectangular tray or tank comprises a bottom, a first wall parallel to a third side and a second wall parallel to a fourth wall, wherein each wall has an inner and an outer surface and wherein the tray is dimensioned to contain an electrophoresis gel, and wherein the wall are essentially transparent to one or more light sources is attached to the external surface of at least one of the walls and is positioned to illuminate an edge of an electrophoresis gel disposed within the vessel. The light source provides one or more of the excitation wavelengths required effect the emission portions of fluorescence by fluorophores contained within the gel allowing the fluorescence to be visualized. In certain embodiments such visualization is achieved without the use of an optical filter while in other embodiments a single optical is utilized to aid visualization of the fluorescence. In certain embodiments wherein an optical filter is utilized the filter is disposed between the gel and a viewer or a light detection instrument. In preferred embodiments the light emitted by the fluorophore is of sufficient intensity to be detectable by the viewer's unaided eye or alternatively by an optical instrument such as a camera or optical scanner. In certain preferred embodiments the apparatus is a vessel equipped to perform standard analytical or preparative electrophoreses procedures. Such an embodiment permits observation and/or recording of the fluorophore patterns in an electrophoreses gel as the electrophoresis procedure is running.

DESCRIPTION OF THE INVENTION

The apparatuses and methods of the present invention are useful for the visualization of fluorophores in biological systems.

In certain embodiments, the invention presents an innovative method for viewing and cutting-out DNA bands from a preparative gel after electrophoretic separation. The apparatuses comprise a container such as a tray designed for viewing an electrophoresis gel or a vessel designed for preparative gel electrophoresis applications. Such embodiments are particularly suitable for visualization of DNA bands of concentrations in the range 10 nanograms or less, which have been stained with fluorescent dyes having excitation wavelengths between 480 nm and 570 nm, depending upon the specific fluorescent dye chosen.

However the method is in no way limited electrophoretically separated to fluorescent dye stained DNA. For example in certain embodiments the apparatuses and techniques of the present invention are useful for the visualization of macromolecules inside cells grown in cell-culture media.

The macromolecules visualized with the devices and methods of the present invention can be naturally fluorescent or can be coupled or stained with any of a variety of fluorescent dyes. There are more than 100 commercially available fluorescent dyes and stains, each applicable for a particular analysis, and all of which are useful in the present invention. A list of particularly useful fluorescent dyes includes, but is not limited to, SYBR® Green (available from Invitrogen Corporation Carlsbad, Calif.) and GelGreen™ (available from Biotium, Inc., Hayward, Calif.), and GelRed™ (available from Biotium, Inc. Hayward, Calif.).

Certain embodiments of the present invention comprise an orthogonal illuminator, which illuminates the edge of an electrophoresis gel for direct viewing of electrophoretically separated nuclei acids stained with fluorescent dyes, wherein a light source is provided by one or more light emitting diodes (LED's) having emissions at or near the excitation wavelength of the dye. In certain preferred embodiments, the apparatus has an LED located at or near at least one of the four corners of a rectangular housing around the viewing area and a light guides is disposed along the sides of the viewing area to be illuminated to aid in diffusion of the light evenly across the edges of the gel being viewed. Ideally, such light guides have a pattern of dimples, or other suitable means for redirecting the illumination from the light sources in the corners uniformly toward the edge of the gel. Generally, the light source is disposed at an approximately 90° angle of incidence (orthogonal) with respect to the plane of a vertical edge of the gel and the light emitted from the dye-stained fluorophores through the top surface of the gel such that the bands can be viewed by looking at the top surface of the gel.

While there is no actual limit to the size of the viewing area of the devices described herein, in certain preferred embodiments the viewing area is approximately 12.5 cm×12.5 cm to accommodate gels so dimensioned or gels of smaller dimensions. Such a configuration allows many common commercial sized gels, such as the Mini, Portrait, Landscape, Medium or Long pre-cast agarose gels and the Landscape PAG & Mini PAG gels (available from Embi Tec, San Diego, Calif.), to be accommodated.

In preferred embodiments, wavelengths emitted by stained nuclei acids range from the deep blue in the range of 440 nm to near infrared in the range of about 660 nm can be viewed directly with the naked eye eliminating the need for an optical filter. Such a technique permits visualization of the fluorescence emitted by the stained double-stranded DNA in quantities as low as approx. 10 nanograms with a suitable optical filter In certain preferred embodiments, gel-separated DNA fragments low-melting agarose afford a suitable image for visualization; gel-separated DNA fragments in regular agarose also afford a suitable image for visualization; and gel-separated DNA fragments in polyacrylamide also afford a suitable image for visualization or photography.

In certain embodiments a transparent gel tray is utilized to hold the gel thereby permitting viewing of the gel-separated DNA fragments in a manner that produces bands that appear much brighter than the bands observed by other methods and in certain of these embodiments the transparent gel tray is water clear.

Another feature of the methods of the present invention over other methods is the utilization of visible light of a wavelength optimized for a particular fluorophore or for a fluorescent particular dye, wherein the visible light causes much less damage to the separated/purified biomolecules than does UV light. The use of visible light permits viewing of the preparative gels with the naked eye and allows for the desired bands of the gel to be cut without exposing the user to harmful UV irradiation. Additionally, photographic images of the gels using such a visualization technique clearly exhibit the separated bands with virtually no distracting background images.

In certain embodiments the light source(s) power controller comprises a dimmer to adjust the intensity of the light for optimum viewing of various concentrations of fluorophores. Certain embodiments incorporate a timing mechanism to periodically illuminate the gel in the tank during an electrophoretic separation process, wherein an interface device is provided to trigger a camera when the gel is illuminated. Certain other embodiments incorporate other control features such as momentary, thermally limited ultra-bright illumination to aid in analysis.

Certain embodiments require two types of control devices, wherein a first control device is used to adjust the intensity of illumination when an operator is examining a gel and a second the control device to adjust the intensity of illumination that allows an operator to select an optimum level for photography. In still other embodiments a timing device is incorporated, wherein such a timing device functions to shut-off the light source after a predetermined period of time in order to prevent photo bleaching of the fluorophores. Also, such a timing device is useful in all cases wherein fluorophore is a non-migrating band of dye-stained DNA. In still other embodiments, the intensity of the light source is controlled by a thermal sensor, thus permitting maximum excitation within the thermal limitations of the gel and the controls.

In certain embodiments, wherein the gel is in an electric field such that the fluorophore is actively moving across the gel, a more complex control is employed. In such embodiments the intensity of the light is adjustable and can be turned on for a brief period to allow an operator or a camera to observe, or a camera to photograph, the progress of the fluorophore as it traverses the gel. In such embodiments the operator can control the timing manually or, as may be the case with a camera operation, the timing can be performed automatically. Commonly in such embodiments provisions are made for the light controller to trigger the camera shortly after initiating the illumination period.

Some classes of gel are virtually water clear, without the cloudiness found in conventional agarose gels. Therefore in yet another embodiment of the invention, UV light is focused to illuminate at least one edge of the gel, exciting the fluorescent dye while restricting the UV from exiting the gel toward the operator due to total internal reflection of the UV. Such an embodiment has an advantage over trans-illumination in that the UV is not directed towards the operator so that the operator is not required to employ a UV safety filter. Such an embodiment also has an advantage over epi-illumination in that a much lower level of illumination is required, minimizing the harmful stray and reflected UV.

Certain embodiments of the apparatus comprise a source of excitation illumination having a wavelength longer than ultraviolet (UV) at or near the band of wave-lengths of a stain for DNA that produces fluorescent illumination at a band of wave-lengths. Since there are a very large number of stains and dyes available, each with its unique range of excitation wavelengths and unique emission wavelengths, each dye or stain requires that the viewing apparatus be tailored to meet its particular parameters. The only common characteristic is that the excitation wavelength is always shorter that the emission wavelength. However, some stains and dyes are sufficiently similar that a single excitation wavelength can be used effectively with one or more stains or dyes. Often, the emission wavelengths are sufficiently different such that different filters might be required for optimum results. Depending on the particular fluorescent dye, the excitation wavelengths range from about 400 nm to about 550 nm, whereas the fluorescence emission wavelengths range from about 500 nm to about 660 nm and are always longer than the excitation wavelengths, in which ranges at least some of the wavelengths of illumination are the same as at least some of the wave-lengths of stain excitation, wherein a light source illuminating at least one edge of an agarose gel, and the source not illuminating any surface of the gel except edges to any material extent, and at least one surface of the gel other than an edge surface available for direct viewing. In such embodiments suitable light sources for excitation illumination include, but are not limited to, one or more light emitting diodes (LED's), Laser Diodes, fluorescent light sources or cold cathode fluorescent lamps (CCFL's) light sources. Also, such embodiments can include a mask to minimize viewing of the excitation illumination that covers the area of illumination not containing the specimen. Such a mask functions to minimize exposure of the operator to the excitation illumination.

Light sources applicable for use in these applications are available from numerous sources including, but not limited to: Nichia (Los Angeles, Calif.) supplier of a Blue LED (Part No. NJSB036BLT), a Green LED (Part No. NS6G083); Kingbright, (City of Industry, Calif.), a Blue LED (APD3224PBC_Z-F01); Cree (Durham, N.C.) a Green-Blue LED (CLM4B-BKW&GKW (995); Z-Bolt (Clackamas, Oreg.) Green Laser (DPSS-20A); Micro Fiber Products (Laguna Niguel, Calif.) Blue Laser (MPO-BPL5 D), Sunlight Lighting (New York, N.Y.) Blue Mini Fluorescent (Model 30350) and Green Mini Fluorescent (Model 30355); and Logisys (Diamond Bar, Calif.), Single Green CCFL (MOD-CCFL-GRE), UV CCFL (MOD-CLK12UV2) and Single Blue CCFL (MOD-CCFL-BL).

Certain preferred embodiments of the apparatus comprise a light source for excitation illumination at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation, wherein the source illuminating at least one edge of an agarose gel, and the source not illuminating any surface of the gel except edges to any material extent, and at least one surface of the gel other than an edge surface available for direct viewing.

In such embodiments a single optical filter may be interposed between the gel and the viewer wherein at least some stray excitation illumination is blocked, but wherein substantially all of the fluorescent illumination is passed.

Certain embodiments of the apparatus comprise a source of excitation illumination other than Ultraviolet at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation, wherein the source illuminating at least one side of an electrophoresis tank containing a gel in an electrical field and the source not illuminating any surface of the gel except at least one edge to any material extent, and wherein at least one surface of the gel other than an edge surface available for direct viewing. In such embodiments a suitable source of excitation illumination is one or more LED's, one or more Laser Diodes, one or more fluorescent light sources or one or more CCFL light sources. In such embodiments a single optical filter may be interposed between the gel and the viewer wherein at least some stray excitation illumination is blocked, but wherein substantially all of the fluorescent illumination is passed.

Certain preferred embodiments of the apparatus comprise a source of excitation illumination other than Ultraviolet at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation, wherein the source illuminating the bottom surface of an agarose gel in a trans-illumination manner and the source not illuminating any surface of the gel except the bottom surface to any material extent and the top surface of the gel available for direct viewing. In such embodiments a suitable source of excitation illumination is one or more LED's, one or more Laser Diodes, one or more fluorescent light sources or one or more CCFL light sources. Also, such embodiments can include a mask to minimize viewing of the excitation illumination that covers the area of illumination not containing the specimen. Such a mask functions to minimize viewing of the excitation illumination.

Certain preferred embodiments of the apparatus comprise a source of excitation illumination other than Ultraviolet at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation; wherein the source illuminating the bottom surface of an agarose gel in a trans-illumination manner, and the source not illuminating any surface of the gel except the bottom surface to any material extent and the top surface of the gel available for direct viewing; and wherein not more than one optical filter is interposed between the gel and the viewer such that at least some of the excitation illumination is blocked, but substantially all of the fluorescent illumination is passed. In such embodiments a suitable source of excitation illumination is one or more LED's, one or more Laser Diodes, one or more fluorescent light sources or one or more CCFL light sources. Also, such embodiments can include a mask to minimize viewing of the excitation illumination that covers the area of illumination not containing the specimen. Such a mask functions to minimize viewing of the excitation illumination.

Certain preferred embodiments of the apparatus comprise a source of excitation illumination other than Ultraviolet at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation; wherein the source illuminating the top surface of an agarose gel in an epi-illumination manner and the source not illuminating any surface of the gel except the top surface to any material extent; and wherein the top surface of the gel available for direct viewing. In such embodiments a suitable source of excitation illumination is one or more LED's, one or more Laser Diodes, one or more fluorescent light sources or one or more CCFL light sources. Also, such embodiments can include a mask to minimize viewing of the excitation illumination that covers the area of illumination not containing the specimen. Such a mask functions to minimize viewing of the excitation illumination.

Certain preferred embodiments of the apparatus comprise a source of excitation illumination other than Ultraviolet at or near the band of wave-lengths of a stain for DNA that produces fluorescent illumination at a band of wave-lengths longer than the wave-lengths of illumination, in which at least some of the wave-lengths of illumination are the same as at least some of the wave-lengths of stain excitation; wherein the source illuminating the top surface of an agarose gel in an epi-illumination manner and the source not illuminating any surface of the gel except the top surface to any material extent; and wherein the top surface of the gel available for direct viewing and not more than one optical filter is interposed between the gel and the viewer such that at least some of the excitation illumination is blocked, but substantially all of the fluorescent illumination is passed. In such embodiments a suitable source of excitation illumination is one or more LED's, one or more Laser Diodes, one or more fluorescent light sources or one or more CCFL light sources. Also, such embodiments can include a mask to minimize viewing of the excitation illumination that covers the area of illumination not containing the specimen. Such a mask functions to minimize viewing of the excitation illumination.

Also in yet other embodiments the gel along at least one edge, since to the extent that the gel is clear, the harmful UV light is confined to the gel. Such an embodiment has an advantage over trans-illumination in that the UV is not directed towards the operator so that the operator is not required to employ a UV safety filter. Such an embodiment also has an advantage over epi-illumination in that a much lower level of illumination is required, minimizing the harmful stray and reflected UV.

FIG. 1 is an orthogonal top view of an illuminator apparatus 10 of the present invention comprising a rectangular tray 11 and having an electrophoresis gel 20 disposed therein for viewing. Illuminator 10 is provided with an array of light sources 12 disposed along an inner wall 14 and a second array of light sources 13 disposed along an inner wall 15. FIG. 2 and FIG. 3 are sectional orthogonal side and end views respectively of the illuminator apparatus 10. FIG. 2 and FIG. 3 clearly illustrate the position of the light source arrays about the periphery of the bottom of the inside of tray 11 such that illumination is directed to pass through the gel edges 21 and 22. FIG. 2 and FIG. 3 also depict an optional optical filter 30 disposed between the upper surface of the gel and the viewer 31 and/or the camera 32. The use of the optical filter 30 is option and, if utilized, may optimize the images of fluorophores in the gel.

FIG. 4 is an isometric view of an illuminator apparatus 50 of the present invention comprising a vessel in the form of a rectangular tray 51 and having an electrophoresis gel 60 disposed therein for viewing. Illuminator 50 is provided with a four light sources 52 individually disposed in a corner of tray 51 wherein the light emitted by each light source 53 is directed through one of the four light guides 54, each of which is positioned along the base of an inner wall of tray 51. Each light guide 54 is position to direct the light emitted from a light source 53 to uniformly illuminate an edge 61 of gel 60. FIG. 5 and FIG. 6 depict side and end orthogonal view respectively of the illuminator 50 of FIG. 4. FIGS. 4, 5 and 6 also depict an optional optical filter 65 disposed between the upper surface of the gel and the viewer 66 and/or the camera 67. The use of the optical filter 65 is option and, if utilized, may optimize the images of fluorophores in the gel.

FIGS. 10a, 10b, 10c, 10d and 10e depict possible arrangements of one, two, three or four light source arrays for embodiments of the present invention wherein the apparatus comprises a rectangular vessel useful for observing and/or recording patterns of fluorescence emitted from fluorophores in a gel medium such as an electrophoresis gel. The light source arrays are disposed on the inner surface of the vessel walls such that illumination from the light sources passes through the edges of the gel to excite the fluorophores therein.

FIGS. 11a, 11b, 11c, 11d and 11e depict possible arrangements of one, two, three or four light source arrays for embodiments of the present invention wherein the apparatus comprises a rectangular vessel equipped to run gel electrophoreses wherein the vessel comprises a tank or tray having one or more walls that are transparent or water clear. The light source arrays are disposed on the outer surface of the vessel walls thereby permitting illumination from the light sources to pass through to excite fluorophores. In such embodiments the fluorescence can therefore be observed and/or recorded during the electrophoresis process.

EXAMPLES

Example 1

Fragments of 600 bp and 1200 bp dsDNA were separated by Gel Electrophoresis loaded as follows:

| Lane #: | 1 | 2 | 3 | 4 | 5 | 6 |
|---|---|---|---|---|---|---|
| DNA loaded (ng): | 500 | 400 | 300 | 200 | 100 | 50 |

Figure 12A:
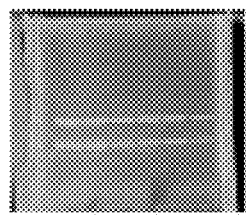
FIG. 12a is an image of a gel-separated DNA seen through an orange filter.
Figure 12B:
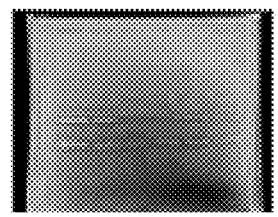
FIG. 12b is an image of a gel-separated DNA seen through a yellow filter.

The gel was illuminated through an edge. FIG. 12a is a photographic image of the gel taken through an orange filter and FIG. 12b is a photographic image of the gel taken through a yellow filter.

Example 2

Fragments of Lamda DNA were separated by Gel Electrophoresis loaded as follows:

| Lane #: | 1 | 2 | 3 | 4 | 5 | 6 |
|---|---|---|---|---|---|---|
| DNA loaded (ng): | 500 | 240 | 125 | 500 | 250 | 125 |

Figure 13A:
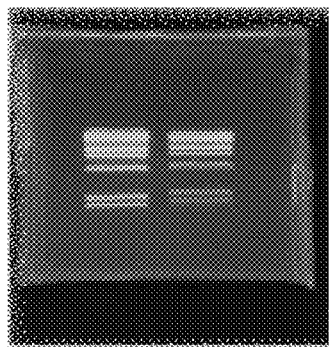
FIG. 13a is an image of a gel-separated DNA seen through an orange filter.
Figure 13B:
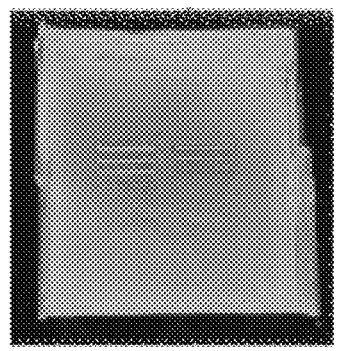
FIG. 13b is an image of a gel-separated DNA seen through a yellow filter.

The gel was illuminated through an edge. FIG. 13a is a photographic image of the gel taken through an orange filter and FIG. 13b is a photographic image of the gel taken through a yellow filter.

Example 3

Figure 14:
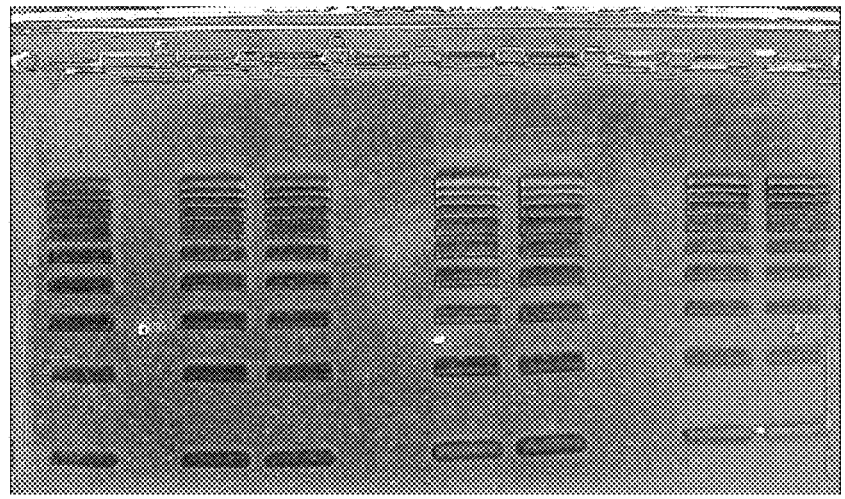
FIG. 14 is an image of a gel-separated DNA stained with Syber Green and seen without a filter.

A photographic image of DNA, separated by Gel Electrophoresis, stained with Syber Green and visualized by edge illumination of the gel using no filter, is presented in FIG. 14.

We claim:

1. An apparatus useful for the visualization of fluorophores in biological systems comprising:
   a vessel configured to contain an electrophoresis gel wherein the electrophoresis gel comprises a top planar surface, a bottom planer surface parallel to the top planar surface and at least first and second planar edges perpendicular to the plane of the top and bottom planar surfaces, the planar edges being adjacent each other in that the first planar edge is contiguous to the second planar edge;
   at least a first light source configured to provide orthogonal illumination to the first planar edge of the electrophoresis gel disposed within the gel vessel such that light emitted from one or more fluorophores within the gel is emitted through the top surface or bottom surface of the gel such that the fluorophores can be visualized by a viewer or an optical instrument placed adjacent to the top or bottom surface of the gel; and
   at least a second light source configured to provide orthogonal illumination to the second planar edge.

2. The apparatus of claim 1 wherein the vessel is a polygonal shaped vessel comprising a base having flat inner surface and a plurality of vertical walls less than or equal to the number of edges of the polygon, wherein each vertical wall has an inner surface and wherein the vessel is dimensioned to contain the electrophoresis gel; and wherein said at least one light source is at least one first vertical wall light source attached to the inner surface of a first vertical wall.

3. The apparatus of claim 1 further comprising one or more optical filters disposed between the top planar surface of the gel and the viewer or the optical instrument such that the optical filter is selected to function as an aid for visualization of fluorescence emitted from the gel.

4. The apparatus of claim 1 wherein said at least one light source is a visible light source.

5. The apparatus of claim 1 wherein said at least one light source is an ultraviolet light source.

6. The apparatus of claim 1 wherein said at least one light source comprises one or more light emitting diodes.

7. The apparatus of claim 2 wherein the shape of the polygonal shaped vessel base is similar to the shape of the base of the gel disposed therein.

8. The apparatus of claim 2 wherein the polygonal shaped vessel base is a rectangular vessel base.

9. The apparatus of claim 2 wherein the second light source is attached to the inner surface of a second vertical wall.

10. The apparatus of claim 9 wherein the first vertical wall and second vertical wall are adjacent.

11. The apparatus of claim 9 wherein the first vertical wall and second vertical wall are opposed.

12. The apparatus of claim 9 further comprising at least one third vertical wall light source attached to the inner surface of a third vertical wall wherein the third vertical wall light source is positioned to provide orthogonal illumination to a third vertical edge of the gel.

13. The apparatus of claim 12 further comprising at least one fourth vertical wall light source attached to the inner surface of a fourth vertical wall wherein the fourth vertical wall light source is positioned to provide orthogonal illumination to a fourth vertical edge of the gel.

14. The apparatus of claim 2 further comprising at least one light guide positioned in proximity to said at least one first vertical wall light source and suitably disposed to diffuse light emitted by the first vertical wall light source evenly across an edge of the gel being viewed.

15. An apparatus useful for the visualization of fluorophores during a gel electrophoresis procedure comprising:
a vessel to perform electrophoreses procedures, the vessel including a rectangular tray or tank comprising a bottom and four walls having an inner and an outer surface and wherein the tray is dimensioned to contain an electrophoresis gel, at least first and second light sources positioned to illuminate respective first and second edges of an electrophoresis gel disposed within the vessel allowing the fluorescence emitted by the gel to be visualized by a viewer or an optical instrument suitable for such visualization from a surface of the gel that is orthogonal to the first and second edges of the gel, the first and second edges of the gel being contiguous and orthogonal to each other.

16. The apparatus of claim 15 further comprising one or more optical filters disposed between the gel and a viewer or an optical instrument wherein that the optical filter functions to aid in detection of fluorescence emitted from a gel therein disposed.

17. An apparatus useful for the visualization of fluorophores comprising:
a vessel comprising a rectangular base having a flat inner surface and one to four vertical walls each disposed along an edge of the rectangular base, wherein each vertical wall has an inner surface and wherein the vessel is dimensioned to contain an electrophoresis gel, said gel comprising parallel planer top and bottom gel surfaces and gel edges disposed orthogonally to the plane of said top and bottom gel surfaces; wherein
at least one vertical wall is provided with one or more light sources positioned to illuminate at least one gel edge of an electrophoresis gel disposed therein; and
wherein said one or more light sources provide one or more of the excitation wavelengths required to effect the emission of fluorescence by fluorophores contained within a gel disposed within the vessel such that the fluorophores can be visualized by a viewer or an optical instrument suitable for such visualization by directed to the top or bottom surface of the gel; and wherein at least one vertical wall is movable with respect to an edge of a gel disposed therein such that the distance between said one or more light sources and the gel edge can be varied to provide a desired illumination intensity.

18. The apparatus of claim 17 further comprising one or more light guides positioned to direct light emitted by said one or more light sources towards one or more edges of a gel disposed therein.

19. The apparatus of claim 17, wherein the gel is rectangular and has first, second, third, and fourth edges, and the apparatus includes at least third and fourth light sources respectively configured to provide light into the third and fourth edges such that all four edges of the gel can be illuminated simultaneously.

* * * * *